United States Patent [19]
Nakano et al.

[11] Patent Number: 5,403,731
[45] Date of Patent: Apr. 4, 1995

[54] PROCESS OF PRODUCING MODIFIED SUPEROXIDE DISMUTASE

[75] Inventors: Yoshiyuki Nakano, Kobe; Hajime Hiratani, Sennan; Kazuo Kato, Kobe, all of Japan

[73] Assignee: JCR Pharmaceuticals Co., Ltd., Hyogo, Japan

[21] Appl. No.: 162,382

[22] Filed: Dec. 3, 1993

Related U.S. Application Data

[63] Continuation of Ser. No. 922,360, Jul. 29, 1992, abandoned, which is a continuation of Ser. No. 608,196, Nov. 2, 1990, abandoned.

Foreign Application Priority Data

Nov. 2, 1989 [JP] Japan ................ 1-286798

[51] Int. Cl.$^6$ .............. C12N 11/08; C12N 11/06; C12N 9/02; C12N 9/04
[52] U.S. Cl. .................. 435/181; 435/180; 435/189; 435/190
[58] Field of Search ............ 435/180, 181, 189, 190

[56] References Cited

U.S. PATENT DOCUMENTS

| | | | |
|---|---|---|---|
| 4,496,689 | 1/1985 | Mitra | 525/54.1 |
| 4,563,349 | 1/1986 | Miyata et al. | 424/94.4 |
| 4,774,185 | 9/1988 | Asami et al. | 435/189 |
| 5,006,333 | 4/1991 | Saifer et al. | 424/78 |

OTHER PUBLICATIONS

Beauchamp et al. (1983) *Anal. Biochem.*, 131, 25–33.
Sanchez-Moreno (1989) *Arch. Microbiol.*, 152, 407–410,
"Superoxide Dismutase in Strains of the genus Flavobacterium: Isolation and Characterization".

*Primary Examiner*—Douglas W. Robinson
*Assistant Examiner*—Jon P. Weber
*Attorney, Agent, or Firm*—Burgess, Ryan & Wayne

[57] ABSTRACT

A modified superoxide dismutase represented by the formula:

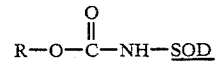

(wherein R is as defined below; SOD is a residue of superoxide dismutase) is produced, in a shortened period of reaction with a high and constant modification ratio, by reacting a polymeric carbonyldiimidazole derivative represented by the formula:

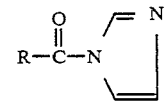

(wherein R is a residue of a water soluble polymer having an average molecular weight of about 2,000 to 10,000) with superoxide dismutase in the presence of a buffer having a pH of 9.0 to 11.0 and a concentration of 0.1 M to 0.5 M, preferably 0.2 M to 0.4 M, at a temperature of 30° to 70° C., preferably 45° to 60° C. The modified superoxide dismutase thus produced exhibits a suitably prolonged blood half-life.

9 Claims, 2 Drawing Sheets

PROCESS OF PRODUCING MODIFIED SUPEROXIDE DISMUTASE

This application is a continuation of application Ser. No. 922,360, filed Jul. 29, 1992, now abandoned, which is a continuation of application Ser. No. 608,196, filed Nov. 2, 1990, now abandoned.

FIELD OF THE INVENTION

This invention relates to modified superoxide dismutases that are utilizable as pharmaceuticals, such as treatment agents of ischemic diseases or radiation hazards, and antitumor agents; in cosmetics intended for use in the prevention of oxygen injuries occurring on the skin; and for other purposes.

BACKGROUND OF THE INVENTION

Superoxide dismutase (SOD) occurs naturally in the biosphere or living world extensively and is known as an enzyme capable of eliminating superoxide anion radicals (hereinafter referred to briefly as "radicals") which are metabolites of oxygen. SOD is found in all and every living beings or organisms that require oxygen for growth, such as animals, plants and microorganisms.

It has been discovered and confirmed in man that SOD exists in three different types; SOD containing copper and zinc, SOD having manganese and extracellular SOD being present outside cells, among which the type containing copper and zinc is widely known to the general public. Reports have been made that such different types of SOD are effective for rheumatism and arthritis deformans, and in expectation of preventing injuries by ischemia- recirculation, for example, clinical trials are currently under way but in most cases through administration of SOD in the unmodified state. In the light of the fact that such types of SOD show a half-life in the blood as short as some minutes after administration, it cannot be said that SOD is allowed to produce its own effects to the maximal extent; in other words, the efficacy testing has been conducted only on a limited scope.

This invention is concerned with a process which can permit modified superoxide dismutases with a high degree of purity having a markedly elongated blood half-life and consequently finding a wide range of clinical application as a drug substance to be produced on a commercial scale in simplified manners and in increased yields. Heretofore, a great variety of chemical modifications have been performed in order to provide SOD with a prolonged half-life in the blood. For example, modification of SOD was made with high-molecular-weight dextrin (W. F. Petrone et al., Proc. Natl. Acad. Sci. U.S.A., 77, 1159 (1980)), polyethylene glycols (The Japanese Unexamined Patent Publication Nos. 249,388/61, 115,280/62 and 245,671/63, and a report by Charles O. Beauchamp et al. (Analytical Biochemistry, 131, 25–33 (1983)) or inulin (The Japanese Unexamined Patent Publication No. 32,826/58). Nevertheless, the said modified SODs as well as the above-mentioned processes for the production of such SODs suffer from various disadvantages to be described below, resulting in failure to solve the problems satisfactorily.

The above-described SOD derivatives have all been developed for the purpose of preventing oxidative tissue injuries in the living body through intravenous and intramuscular administration. Except as stated in the above report by Charles O. Beauchamp et al., all of such derivatives are the high-molecular-weight modified SODs that are produced by use of activated modifying agents having two functional groups with the result that two molecules of SOD are introduced, and consequently, they are provided with an extremley extended half-life in the blood; they present the disadvantage that they remain in the living body for a MUCH TOO long period of time, although they offer the advantage of having a longer blood half-life than unmodified SOD. Beauchamp et al., in their report mentioned previously, described that they succeeded in making improvements on such disadvantage through the activation of N,N'-carbonyldiimidazole (CDI) to thereby supply polyethylene glycol (PEG) with only one functional group. However, the method suffers from the defects that the treatment batch size is too small to conduct the commercial production of modified SOD, particularly the large-volume production of the same for pharmaceutical uses, and that the treatment requires a prolonged length of time.

Taking into consideration the above situation, this invention has been devised after intensive investigation into the large-volume production of SOD modified with polyethylene glycol (hereinafter referred to briefly as "PEG-SOD") or SOD modified with polyoxyethylene glycol.polyoxypropylene glycol.polyoxyethylene glycol (hereinafter referred to briefly as "PEG-PPG-SOD") to thus utilize them in the application fields as pharmaceuticals.

The present inventors, in the course of research activities carried out on the application of proteins to pharmaceuticals, found that prolongation of blood half-lives of proteins can permit the application scope of proteins to be maximized, and have already filed an application for patent covering the efficacy-sustainable type of proteins as per Japanese Unexamined Patent publication No. 59029/59. Unmodified superoxide dismutase (SOD), that is usable in this invention, has in recent years been attracting enhanced attention as a pharmaceutical, and vigorous clinical studies are under progress with SOD.

Taking notice of the facts that unmodified SOD shows a blood half-life as short as some minutes in rats and that SOD elicits drug efficacy at by far larger doses than generally considered for the enzymatic proteins for medicinal uses, however, the present inventors have conducted repeatedly intensive research on a simplified method, as a means of eliminating such defects, of producing high-purity modified dismutase in improved yields that can realize the large-volume treatment. As described in the above, Beauchamp et al. reported the SOD modified with PEG activated by CDI but their produciton method is encountered with difficulties in conducting into practice for large-scale production in terms of facilities.

SUMMARY OF THE INVENTION

The present invention, being intended to overcome such difficulties, is concerned with a process of producing modified superoxide dismutases represented by the formula:

(wherein R is as defined below; SOD is a residue of superoxide dismutase), characterized in that said process comprises reacting a polymeric carbonyl-diimidazole derivative represented by the formula:

(wherein R is a residue of a water-soluble polymer having an average molecular weight of 2,000 to 10,000) with superoxide dismutase at a temperature of 30° to 70° C., preferably 45° to 60° C., in the presence of a buffer having a pH of 9.0 to 11.0 and a concentration of 0.1M to 0.5, preferably 0.2 to 0.4 M.

DETAILED DESCRIPTION OF THE INVENTION

Figure 1:
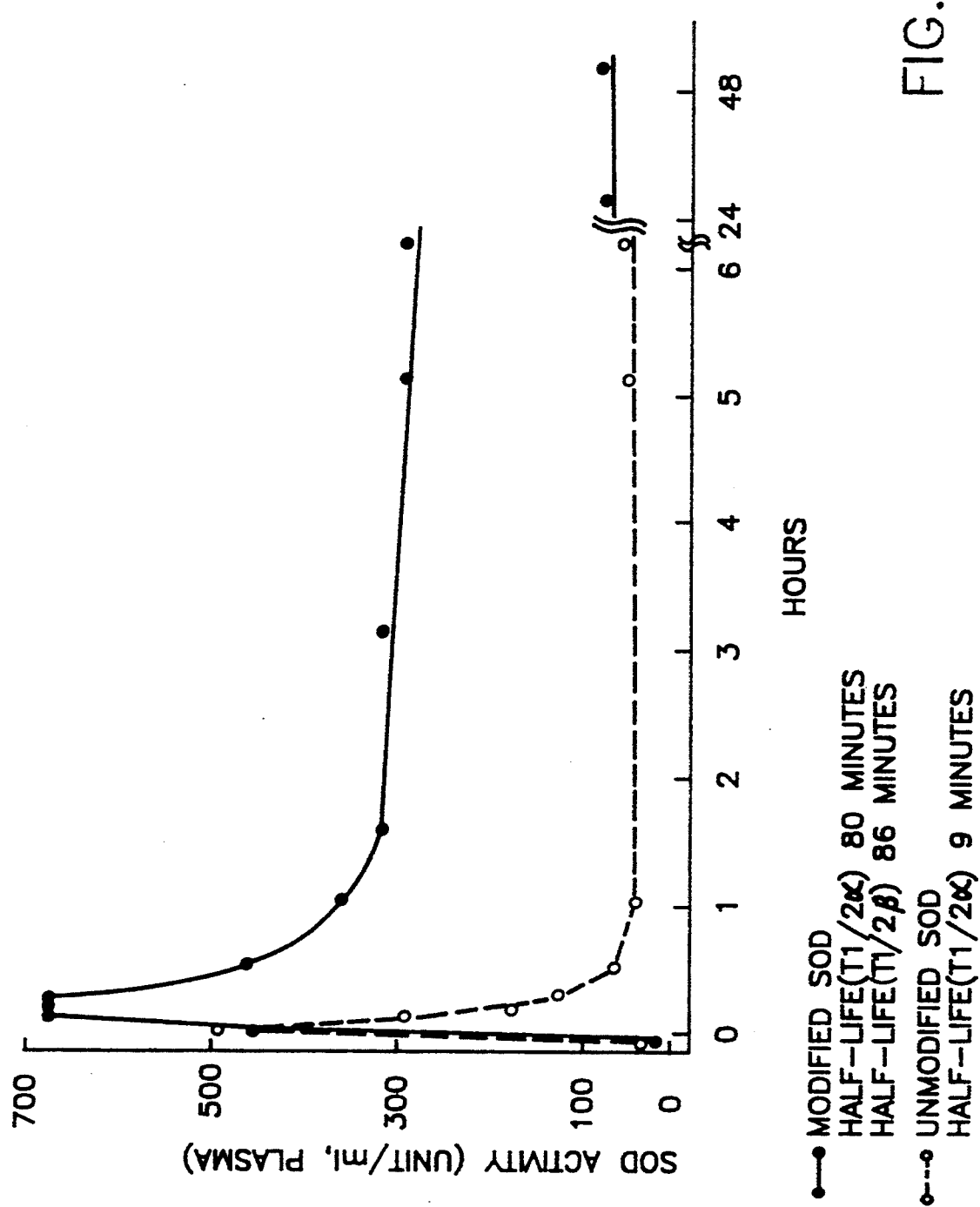
FIG. 1 is a graph showing the time-course changes of the blood levels of modified and unmodified superoxide dismutases in the animal experiment as described in Experiment Example 1.
Figure 2:
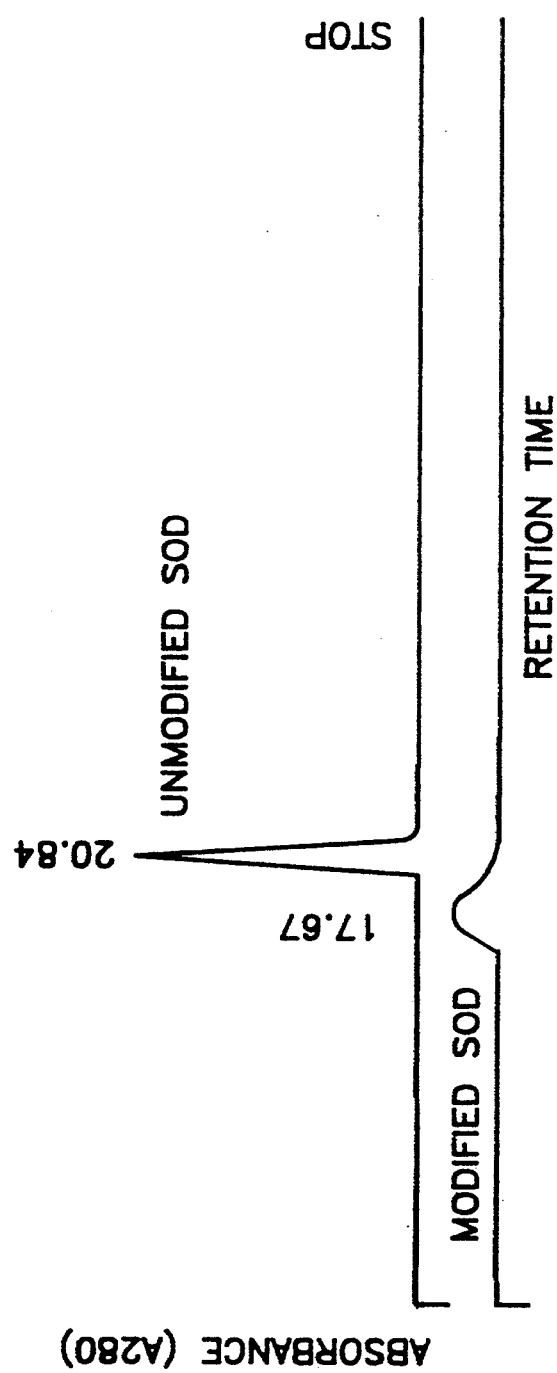
FIG. 2 is a spectrophotogram of the modified superoxide dismutase as purified through gel permeation in Example 1.

The polymeric carbonylinidazole of the formula (I) can be obtained by reacting a water-soluble polymer having a molecular weight of about 2,000 to 10,000 with carbonyldiimdiazole (CDI) in an inert solvent such as dioxane.

As the water-soluble polymer, there may be mentioned, for example, polyoxyalkylene glycols having a molecular weight of about 2,000 to 10,000, such as polyoxyethylene glycols, mono-lower-alkoxypolyoxyethylene glycols and mono-lower-alkoxypolyoxyethylene.-polyoxypropylene.polyoxyethylene glycols. The above-mentioned lower axhoxys usually are $C_1$ to $C_4$ alkoxy groups. Preferred examples of the water-soluble polymer include monomethoxypolyoxyethylene glycols having an average molecular weight of 3,500 and monomethoxypolyoxyethylene.polyoxypropylene.-polyoxyethylene glycols having the same molecular weight.

In order to increase and also maintain at the increased, fixed level a ratio of activation of the water-soluble polymer with CDI, the water-soluble polymer desirably is added into a reaction solvent in such a quantity as its initial concentration may range from 0.15 to 0.35M, preferably from 0.25 to 0.3M, while an initial concentration ratio of the polymer to CDI being at 1:1 to 3, preferably 1:1.5 to 2.5.

Choice of the above concentrations can lead to reduced volume of the reaction solution.

Also, the ratio of activation of the polymer can be maintained at a fixed level through addition of a weakly acid buffer having a pH range of 6 to 6.5 to the reaction mixture to thereby allow the reaction to discontinue without increasing its pH.

After conclusion of the reaction, the derivative the formula (I) can be separated from the reaction mixture by use of such separatory means as dialysis and lyophilization.

Table 1 shows the comparison of an example with this invention and the method of Beauchamp et al. The decided differences between the process of the present inventors and the one of Beacuhamp et al. lie in the concentration of the modifying agent as well as the discontinuation of the reaction through addition of a buffer without bring about an increase in pH value, as employed and effected individually in the production of the activated modifying agent being shown in (A) of Table 1. In the course of intensive research on the improvement of reaction conditions, it has been turned out that the improvement of the said two conditions are essential for the stable large-scale production of the activated modifying agent; namely, the optimally increased concentration of the modifying agent facilitates the activation in large quantities. The range of the concentration can be selected from 0.15 to 0.35M, preferably from 0.25 to 0.3M. Although Beuchamp et al. conducted investigation at 1:10 of the concentration ratio of the modifying agent to the activating agent CDI, the present inventors found out that when the said concentration ratio is maintained at 1:1 to 1:3, preferably 1:1.5 to 1:2.5, the modification can best be performed constant. Also, the increased concentration of the modifying agent can permit the volume of reaction solution to be reduced. This enables the utilization of the equipment capable of concentrating furthermore the reaction solution after conclusion of the reaction, resulting in simplified subsequent treatment steps. Table 1 (B), in which the modification of SOD with activated PEG or PEG-PPG is described, can elucidate more clearly the characteristic features of this invention. According to this invention, it has been proven that the increased concentration of the buffer makes it possible to minimize a change in pH due to a varying amount of the protein and furthermore that a rise in pH can accelerate the reaction rate. The buffer desirably shows a pH of 9 to 10 and a concentration of 0.1 to 0.5M, preferably 0.2 to 0.4M. The composition of the buffer is not particularly limited,, only if the buffer can have the buffering capacity over the pH range of this invention and can be easily prepared. Sodium carbonate buffer is preferable, because it is often used as an additive for pharmaceutical preparations and is considered highly safe. The present inventors carried out extensive investigation into a large-scale production process in which the modification of conclusion of the reaction, resulting in simplified subsequent treatment steps. Table 1 (B), in which the modification of SOD with activated PEG or PEG-PPG is described, can elucidate more clearly the characteristic features of this invention. According to this invention, it has been proven that the increased concentration of the buffer makes it possible to minimize a change in pH due to a varying amount of the protein and furthermore that a rise in pH can accelerate the reaction rate. The buffer desirably shows a pH of 9 to 10 and a concentration of 0.1 to 0.5M, preferably 0.3 to 0.4M. The composition of the buffer is not particularly limited, only if the buffer can have the buffering capacity over the pH range of this invention and can be easily prepared. Sodium carbonate buffer is preferable, because it is often used as an additive for pharmaceutical preparations and is considered highly safe. The present inventors carried out extensive investigation into a large-scale production process in which the modification reaction of SOD with activated PEG or PEG-PPG can be proceeded faster, and as a result, found that the reaction at temperatures of 30° to 70° C., preferably 45° to 60° C., can lead to completion of the modification within a extremely shortened period of time. For other proteins not necessarily being heat-stable, heretofore, it has been considered undesirable to allow the modification reaction to proceed at the above-described high temperatures, but this invention has unexpectedly brought excellent results. Furthermore, the present inventors found that the modification reaction can be carried out with the concentrations of both activated PEG or PEG-PPG and SOD being increased, thus making the commercial, large-scale production practically feasible. In view of the fact that this invention is originally intended for the production of PEG or PEG-PPG modified SOD, it is not desirable to produce the modified SOD contaminated with unmodified SOD or activating agent. As a countermeasure against the former, therefore, the present inventors found

TABLE 1

| Comparison of this invention with the method of Beauchamp et al. | | |
|---|---|---|
| | This invention | Beauchamp et al |
| (A) Activation of PEG with CDI | | |
| Solvent | Dioxane | Dioxane |
| Modifying agent | PEG-PPG | PEG |
| Concn. of modifying agent | 300 mM | 50 mM |
| Concn. of activating agent (CDI) | 600 mM | 500 mM |
| Temperature | 30° C. | 37° C. |
| Reaction time | 2 hrs. | 2 hrs. |
| Concentration treatment (evaporator) | Employed | Not employed |
| Discontinuation of reaction | Addition of buffer | |
| Dialysis (outer soln.) | Water | Water |
| Lyophilization | Employed | Employed |
| Ratio of activation | >9 | 6 to 8 |
| (B) Activation of SOD with activated modifying agent | | |
| Buffer | 100 to 500 mM sodium borate (pH 9.5) or sodium carbonate (pH 9.5) | 10 mM sodium borate (pH 8.5) |
| Concn. of activated modifying agent | 5.0 to 100 mM | 180 mM |
| Concn. of SOD | 1 to 2 mM | 0.05 mM |
| Reaction temp. | 40 to 60° C. | 4° C. |
| Reaction time | 0.5 to 1 hrs. | 48 to 98 hrs. |
| No. of modification | Once to twice | Once |
| Purification | DAEA chromato. | Unknown |
| Ratio of modification | 17 to 20% | 5 to 10% |
| Blood half-life | 14 hrs. | 9 hrs. |
| Retention of SOD activity | 92 to 98% | 95% | that twice repeated modification reactions can result in complete disappearance of unmodified SOD, although even once modification reaction yields modified SOD with less than 8% in. content of unmodified SOD being satisfactorily usable in the application fields as pharmaceuticals. Furthermore, it was discovered that anion exchanger column chromatography is a means being effective for the entire elimination of contamination with unreacted activating agent. Since the unmodified activating agent and the modified SOD have individually different molecular weights of 32,000 and 130,000, it usually is a common practice to employ molecular sieve column chromatography, but the present inventors found that anion exchanger column chromatography, being more efficient, is best suited for the said purpose. As the anion exchanger being utilizable to this effect, use can be made of any anion exchangers, only if they possess DEAE groups, but preferably DEAE-Sepharose CL-6B may be usable. It was found out that the SOD being modified in this manner with activated PEG or PEG-PPG shows a ratio of modification as constant as 17 to 20% and that such modified SOD can be produced more efficiently than in the case of the method of Beauchamp et al. when, a chemical compound is intended for use as a pharmaceutical, considered to be the most desirable is the production process being capable of securing the constant, and in the light of the characteristics as described above, the process according to this invention can be said to fully meat such requirement.

SOD that is usable in this invention is not particularly limited in terms of its origin or source, but is desirably SOD containing copper and zinc.

Below described are, the experiment examples as well as the samples, whereby the determination or analytical methods employed are to be given in the first place.

Assay of SOD activity

Employed was the procedure of McCord and Fridovich (J. C. B., 244, 6049–60551,(1969)), according to which procedure in the superoxide generating system with xanthine-xanthine oxidase where cytochrome C and unmodified SOD or modified SOD were allowed to coexist, the amount of either of such unmodified or modified SOD to lower a rate of cytochrome C reduction was determined as an index for assaying the enzymatic activity. The retention (%) of the enzymatic activity of modified SOD was expressed in terms of a proportion on the basis of the enzymatic activity (taken as 100%) of unmodified SOD as assayed against the superoxide generated in the xanthine-xanthine oxidase system.

Determination of ratio of modification

To a 0.6M boric acid.sodium hydroxide buffer having a pH of 9.5 were added 0.1 ml of unmodified SOD, 0.1 ml of 0.2N sodium hydroxide reagent solution and 0.1 ml of sodium 2,4,6-trinitrobenzenesulfonate (7.2 mg/ml of water, referred to as "TNBS"), and the reaction was allowed to proceed over a water bath for 3 hours at 25° C. The reaction solution was subjected to measurement of absorbance at a wavelength of 367 nm. The amount of protein is plotted as abscissa and the absorbance as ordinate to prepare a calibration curve (an inclination: A) for TNBS coloration of unmodified SOD. The same procedure was repeated with modified SOD to prepare a calibration curve (an inclination: B) for TNBS coloration of modified SOD. The ratio (%) of modification was calculated by the equation of $[(A-B)/A] \times 100$.

Determination of molecular weight

Determination of molecular weights was carried out by means of high-performance liquid chromatography (HPLC) with use of TSK G 3000 SW (produced by Toso K. K. of Japan); chromatography was conducted while utilizing as a solvent 0.1M sodium phosphate buffer of pH 7.0 containing 0.3M sodium chloride flowing at a rate of 1.0 ml/min.

Analysis by electrophoresis

With use of First System (supplied by Pharmacia Co.), 8 to 25% polyacrylamide concentration-gradient gel electrophoresis was performed, whereby the protein was stained with Coomassie Brilliant Blue R-250.

Quantitative determination of proteins

According to the biuret method of A. G. Cornall et al. (J. B. C., 177, 751 (1949)), the protein was reacted with divalent copper under alkaline conditions, and the resulting red-purple reaction solution was subjected to measurement of absorbance at a wavelength of 540 nm. The protein was determined quantitative through calculation from a calibration curve prepared with bovine serum albumin used as a standard.

EXPERIMENT EXAMPLE 1

Half-life in the blood

House rabbits, being used as experimental animals, were given intravenously SOD modified with PEG-PPG (a molecular weight of 3,500) and unmodified SOD, as replaced with or dissolved in isotonic saline, at a dose of 38,000 units per 2.5 kg body weight, respectively, followed by time-course determination of the serum SOD levels. The results (obtained with two house rabbits) are shown in FIG. 1, which indicates that the modified SOD, showing a lowered rate of blood clearance as compared with unmodified SOD, extended a length of the time of SOD activity development in the blood. However, this does not necessarily mean that the modified SOD resides in the blood forever; as its blood level dropped 24 hours later to about the one prior to administration, the modified SOD was thought to be cleared from the blood and to be then excreted. This fact is considered to be of utmost importance, since it demonstrates that the process was able to produce the modified SOD that was provided with a suitably extended, but not excessively prolonged, SOD activity life-time as compared with unmodified SOD.

Experiment Example 2

Antigenicity

In accordance with the procedure as described in Journal of Immunological Methods, 14, 381 (1977), the modified SOD was tested to find out whether or not it would develop any novel type of antigenicity. Unmodified SOD or modified SOD (ca. 30 ug each) was emulsified with Freund Complete Adjuvant (FCA) and was given A/J mice intraperitoneally, followed by additional administration on Day 14 and Day 28 for immunization. Blood samples were drawn from the mice through the ocular vein in the time course manner at the interval of one week starting with the day of initiation of injection to separate the sera, and the sera after being diluted in advance were given rats through intradermal injection (0.1 ml), followed by intravenous injection of 2 ml of a mixed solution of unmodified SOD (0.5 mS) and Evans blue dye (20 mg) 4 hours later to thus conduct an assessement test for the production of antibody through the passive cutaneous anaphylaxis reaction (PCA reaction) wherein the judgement was made on the basis of vascular permeability of the dye. The results are shown in Table 2, where the figures designate the maximum dilution multiples of the sero at which the PCA reaction turned positive; namely, their larger numeical values mean stronger antigenicity.

TABLE 2

| | Antigenicity tests | | | | |
|---|---|---|---|---|---|
| | No. of animals | PCA - Titer | | | |
| | | Day 7 | Day 14 | Day 21 | Day 28 | Day 35 |
| Unmodified SOD | 10 | 8 | 32 | 128 | 256 | 256 |
| Modified SOD | 10 | 0 | 0 | 0 | 0 | 0 |

The results as shown in Table 2 indicate that unmodified SOD, becasue of its human source, elicited antigenicity, whereas the modified SOD:as produced in accordance with this invention did not produce antigenicity in every animals; this experiment, where SOD of human source was used in the animals of a different species, demonstrated that the modification caused a reduction in the proper antigenicity of human SOD.

EXPERIMENT EXAMPLE 3

Shown in Table 3 are the comparisons in specific activity of unmodified SOD with different modified SOD as produced in the examples.

TABLE 3

| Sample | U/mg protein |
|---|---|
| Unmodified SOD | 3,800 |
| Modified SODs: | |
| Example 1 | 3,800 |
| Example 2 | 3,800 |
| Example 3 | 4,100 |
| Example 4 | 4,100 |
| Example 5 | 3,800 |

All modified SODs were found mot to bring about any reduction in specific activity, which is in sharp contrast to unmodified SOD. This means that the production process according to this invention was able to retain the superoxide anion radical eliminating effect of SOD as was in the natural state, and the finding, coupled with the results of Experiment Example 1, demonstrates definitely that modified SOD having a half-life in the living body alone prolonged was able to be produced.

EXAMPLE 1

(1) Production of monomethoxy polymer:

Into 100 ml of dioxane were 100 g of monomethoxypolyoxyethylene glycol.polyoxypropylene glycol.polyoxyethylene glycol (an average molecular weight of 3,500, produced by Toho Chemical Co. of Japan. EO: PO: EO=1500:500:1500. hereinafter referred to as "OMe-PEG-PPG") and 10 g of carbonyldiimidazole (hereinafter referred to as "CDI"), and the mixture was stirred for 2 hours at 30° C. to produce a solution and simultaneously to allow the reaction to proceed, resulting in a reaction solution containing a CDI derviative of OMe-PEG-PPG (hereinafter referred to as "CDI-PEG-PPG"). In order to remove the dioxane from the reaction solution, the reaction solution was concentreated under reduced pressure over a water bath at a temperature of lower than 30° C. to give about 110 ml of a highly viscous concentrate, to which 0.5M sodium phosphate buffer (pH 6.5) was then added to make up to 200 ml. The diluted solution was subjected to dialysis treatment (the outer solution: water) to give 1,000 ml of the sample solution, followed by lyophilization to produce CDI-PEG-PPG in the form of dried powder, which was stored at −30° C. Yield of 98%.

(2) Production of SOD modified with PEG-PPG:

To a reaction vessel containing 100 ml of 0.3M sodium carbonate buffer (pH 9.5) was added 5 g of lyophilized SOD in such a manner as its final concentration might be at 50 mg/ml, and stirring was performed while immersing the reaction vessel into a constant-temperature bath controlled at a temperature of 50° C. Then, 17.5 g of CDI-PEG-PPG as produced under the previous section (1) was added to the mixture, followed by further addition of the same amount of CDI-PEG-PPG. After the reaction was continued for about 30 min, the reaction solution was subjected to dialysis (the outer solution: water) to give a solution containing crude PEG-PPG-SOD.

(3) Purification of a solution of crude PEG-PPG-SOD:

The solution of crude PEG-PPG-SOD, as produced under the section (2), was pouted for adsorption into a column packed with DEAE-Sepharose CL-6B (produced by Pharmacia Co.) which had been equilibrated through thorough washing with a sufficient volume of water, and the column was washed with water of five times the volume of the column to remove unreacted CDI-PEG-PPG. The adsorbed PEG-PPG-SOD was eluted with 0.3M sodium carbonate-hydrochloric acid buffer (pH 9.5), and the eluate was concentrated through ultrafiltration.

(4) Reaction of SOD re-modified with PEG-PPG:

Because the PEG-PPG-SOD as produced under the section (3) was found to contain 6 5 of unreacted SOD, the concentrate obtained through ultrafiltration under the section (3) was adjusted to a concentration of 50±5 mg/ml and subjected to the same procedure as performed under the section (2) to give a crude solution of SOD completely modified with PEG-PPG, which was then chromatographed on a column of DEAE-Sephrose by the same procedure as described under the section (3). The elution was performed with 25 mM sodium phosphate buffer (pH 7.0) containing 0.9% sodium chloride, and the eluate was concentrated through ultrafiltration and sterile-filtered to give a pure PEG-PPG-SOD solution. Yield of 4.8 g or 96%. The product was found to be a pure and single compound as evidenced by TSK G 3000SW gel permeation and electrophoresis analyses.

EXAMPLE 2

(1) Production of monomethoxy polymer:

To 500 ml of dioxane were added 500 g of OMe-PEG-PPG as described in Example 1 and 50 g of CDI, and the mixture was stirred for 2 hours at 30° C. to produce a solution and simultaneously to allow the reaction to proceed, thereby resulting in a reaction solution containing a CDI derivative of PEG-PPG (CDI-PEG-PPG). In order to remove the dioxane from the reaction solution, the reaction solution was concentrated under reduced pressure over a water bath at a temperature of lower than 30° C. to produce about 600 ml of a highly viscous concentrate, followed by addition of 0.5M sodium phosphate buffer (pH 6.5) to dilute to 1000 ml. Furthermore, the diluted solution was subjected to dialysis treatment (the outer solution: water) to give 5000 ml of a sample solution, followed by lyophylization to produce CDI-PEG-PPG in the form of dried powder. The product was stored at −30° C. Yield of 99%.

(2) Production of superoxide dismutase modified with PEG-PPG:

Into a reaction vessel containing 500 ml of 0.3M sodium carbonate buffer (pH 9.5) was added 30 g of SOD in scuh a manner as its final concentration might be at 60 mg/ml, and stirring was performed while immersing the reaction vessel in a constant-temperature bath controlled at a temperature of 55° C. 87.5 g of CDI-PEG-PPG as produced under the section (1) was added to the mixture, followed by further addition of the same amount of CDI-PEG-PPG 30 minutes later. After the reaction was continued for about 30 minutes, the reaction solution was subjected to dialysis treatment (the outer solution: water) to give a crude PEG-PPG-SOD solution.

(3) Purification of the crude PEG-PPG-SOD solution:

The crude PEG-PPG-SOD solution as obtained under the section (2) was poured for adsorption into a column packed with DEAE-Sepharose CL-6B (produced by Pharmacia Co.) which had been equilibrated through thorough washing with sufficient volume of water, and the column was washed with water offive times the volume of the column to remove unreacted CDI-PEG-PPG. The adsorbed PEG-PPG-SOD was eluted with 0.3M sodium carbonate buffer (pH 9.5), and the eluate was concentrated through ultrafiltration.

(4) Reaction of SOD re-modified with PEG-PPG:

Because the SOD modified with PEG-PPG as produced under the section (3) was found to contain 1.5% of unreacted SOD, the concentrate obtained; through ultrafiltration under the section (3) was adjusted to a concentration of 50±5 mg/ml and subjected to the same procedure as described in the section (2) to give a crude solution of SOD completely modified with PEG-PPG. The crude PEG-PPG-SOD solution was chromatographed on a column of DEAE-Sepharose in the same manner as described under the section (3), followed by elution with 2.5 mM sodium phosphate buffer (pH 7.0) containing 0.9% of sodium chloride, and the eluate was comcentrated through ultrafiltration and sterile filtered to give a pure PEG-PPG-SOD solution. Yield of 29 g or 97%. The product was found to be pure and single compound as evidence by electrophoresis analysis.

EXAMPLE 3

(1) Production of monomethoxy polymer:

Into 100 ml of dioxane were added 100 g of monomethoxy-polyoxyethylene glycol 9an average molecular weight of 3,500, produced by Toho Chemical Co. hereinafter referred to as "OMe-PEG") and 10 g of CDI, and stirring was performed to produce a solution and simultaneously to allow the reaction to proceed, resulting in a reaction solution containing a CDI derivative of PEG (CDI-PEG) In order to remove the dioxane from the reaction solution, the reaction solution was concentrated under reduced pressure over a water bath at a temperature of lower than 30° C. to give about 105 ml of a highly viscous concentrate, to which 0.5M sodium phosphate buffer (pH 6.5) was added to make up to 180 ml. Furthermore, the diluted solution was subjected to dialysis treatment (the outer solution: water) to give 950 ml of a sample solution, followed by lyophilization to produce CDI-PEG in the form of dried powder. The product was stored at −30° C. Yield of 98%.

(2) Production of superoxide dismutase modified with PEG:

Into a reaction vessel containing 100 ml of 0.3M sodium borate buffer (pH 9.5) was added 5 g of lyophilized SOD in such a manner as its finalconcentration might be at 50 mg/ml, and stirring was performed while immersing the reaction vessel in a contant-temperature bath controlled at a temperature of 50° C. 17.5 g of CDI-PEG as produced under the section (1) was added to the mixture, followed by further addition of the same amount of CDI-PEG 30 minutes later. After the reaction was continued for about 30 minutes, the reaction solution was subjected to dialysis treatment (the outer solution: water) to give a crude PEG-SOD solution.

(3) Purification of crude, PEG-SOD solution:

The crude PEG-SOD Solution as obtained under section (2) was poured for adsorption into a column packed with DEAE-Toyo Pearl (produced by Toso Inc. of Japan) which had been equilibrated through thorough washing with sufficient volume of water, and the column was washed with water of five times the volume of the column ro remove unreacted CDIPEG. The adsorbed PEG-SOD was eluted with 0.3M sodium carbonate buffer (pH 9.5), and the eluate was concentrated through ultrafiltration.

(4) Reaction of SOD re-modified with PEG:

Because the PEG-SOD as produced under the section (3) was found to contain about 7% of unreacted SOD, the concentrate obtained through ultrafiltration under the section (3) was adjusted to a concentration of 50±5 mg/ml and subjected to same procedure as described under the section (2) to give a crude solution of SOD completely modified with PEG. The crude PEG-SOD solution was further chromatographed on a column of DEAE-Toyo Pearl in the same manner as described in the section (3), followed by elution with 25 mM sodium phosphate buffer (pE 7.0) containing 0.9% of sodium chloride., and the eluate was concentrated through ultrafiltration and sterile filtered to give a pure PEG-SOD solution. Yield of 4.9 g or 98%. The product was found to be a pure and single compound as evidenced by gel permeation on TSKG 3000 SW and electrophoresis.

EXAMPLE 4

(1) Production of monomethoxy polymer:

Into 200 ml of dioxane were added 200 g of PEG-PPG (an average molecular weight of 7,000) as used in Example 1 and 20 g of CDI, and stirring was effected for 2 hours at 30° C. to produce a solution and simultaneously to allow the reaction to proceed, resulting in a reaction solution containing a CDI derivative of PEG-PPG (CDI-PEG-PPG). In order to remove the dioxane from the reaction solution, the reaction solution was concentrated under reduced pressure over a water bath at a temperature of lower than 30° C. to give about 230 ml of a highly viscous concentrate, to which 0.5M sodium phosphate buffer (pH 6.5) was added to make up to 400 ml. Furthermore, the diluted solution was subjected to dialysis treatment (the outer solution: water) to give 1900 ml of a sample solution, followed by lyophilization to produce CDI-PEG-PPG in the form of dried powder. The product was stored at −30° C. Yield of 94%.

(2) Production of SOD modified with PEG-PPG:

Into a reaction vessel containing 150 ml of 0.3M sodium carbonate buffer (pH 9.5) was added 10 g of lyophilized SOD in such a manner as its final concentration might be at 100 mg/ml, and stirring was performed while immersing the reaction vessel in a constant-temperature bath controlled at a temperature of lower than 50° C. Then, 35g of CDI-PEG-PPG as produced under the section (1) was added to the mixture, followed by further addition of the same amount of CDI-PEG-PPG 30 minutes later. After the reaction was continued for about 30 minutes, the reaction solution was subjected to dialysis treatment (the Outer solution: water) to give a crude PEG-PPG-SOD solution.

(3) Purification of the crude PEG-PPG-SOD solution:

The crude PEG-PPG-SOD solution as obtained under the section (2) was poured for adsorption into a column packed with DEAE-Sepharose CL-6B (produced by Pharmacia. Co.) which had been equilibrated through thorough washing with sufficient volume of water, and the column was washed with water of five times the volume of the column to remove unreacted CDI-PEG-PPG. The adsorbed PEG-PPG-SOD was eluted with 0.3M sodium carbonate buffer (pH 9.5), and the eluate was concentrated through ultrafiltration to give about 220 ml of a concentrate, followed by sterile filtration to give 9.85 g of modified SOD solution. Yield of 98,.5%. Gel permeation on TSKG 3000 SW and electrophoresis showed that unreacted SOD was not detected at all.

EXAMPLE 5

(1) Production of monomethoxy polymer:

Into 100 ml of dioxane were added 100 g of PEG-PPG (an average molecualr weight of 1,750) as used in Example 1 and 10 g of CDI, and stirring was performed for 2 hours at 30° C. to produce a solution and simultaneously to allow the reaction to proceed, resulting in a reaction solution containing a CDI derivative of PEG-PPG (CDI-PEG-PPG). In order to remove the dioxide from the reaction solution, the reaction solution was concentrated under reduced pressure over a water bath at a temperature of lower than 30° C. to give 100 ml of a highly viscous concentrate, to which 0.5 M sodium phosphate buffer (pH 6.5) was added to make up to 200 ml. Furthermore, the diluted solution was subjected to dialysis treatment (the other solution: water) to give 1000 ml of a sample solution, followed by lyophilization to produce CDI-PEG-PPG in the form of dried powder. The product was stored at −30° C.

(2) Production of SOD modified with PEG-PPG:

Into a reaction vessel containing 100 ml of 0.3M sodium carbonate buffer (pH 9.3) was added 5 g of lyophilized SOD in such a manner as its final concentration might be at 50 mg/ml, and stirring was effected while immersing the reaction vessle in a constant-temperature bath controlled at a temperature of 50° C. Then, 17 g of CDI-PEG-PPG as produced under the section (1) was added to the mixture, followed by further addition of same amount of CDI-PEG-PPG 30 minutes later. After the reaction was continued for about 30 minutes, the reaction solution was subjected to dialysis tretment (the outer solution: water) to give a crude PEG-PPG-SOD solution.

(3) Purification of the crude PEG-PPG-SOD solution:

The crude PEG-PPG-SOD solution as obtained under the section (2) was poured for adsorption into a column packed with DEAE-Sepharose CL-6B (produced by Pharmacia Co.) which had been equilibrated through thorough washing with sufficient volume of water, and the,column was washed with water of five times the volume of column to remove unreacted CDI-PEG-PPG. The adsorbed PEG-PPG-SOD was eluted with 0.3M sodium carbonate buffer (pH 9.5), and the eluate was concentrated through ultrafiltration to give 115 ml of a concentrate, followed by sterile filtration to give 4.89 g of a modified SOD solution. Yield of 97.8%. Gel permeation on TSK G 3000 SW and electrophoresis showed that unmodified SOD was not detected at all.

We claim:

1. A process for producing a modified superoxide dismutase represented by the formula:

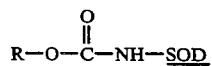

wherein R is as defined below and SOD is a residue of superoxide dismutase, said process comprising reacting a water-soluble polyoxyalkylene polymer having a molecular weight of 2,000 to 10,000 with carbonyldiimidazole in the respective concentrations of 0.15 to 0.35M and 0.15 to 1.05M and at a concentration ratio of 1:1 to 1:3. followed by discontinuation of the reaction through addition of a buffer without bringing about an increase in pH to produce a polymeric carbonylimidazole represented by the formula:

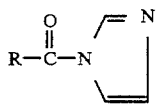

wherein R is a residue of the polyoxyalkylene polymer, and reacting the polymeric carbonylimidazole with a superoxide dismutase in the presence of a buffer, which buffer has a pH of 9.0 to 11.0 and a concentration of 0.1 to 0.5M, at a temperature of 30° to 70° C. for a sufficient length of time to form the modified superoxide dismutase.

2. A process as described in claim 1, wherein the carbonylimidazole is a carbonylimidazole of monomethoxypolyoxyethylene glycol having an average molecular weight of 3,500.

3. A process as described in claim 1, wherein the carbonylimidazole is a carbonylimidazole of monomethoxypolyoxyethylene polyoxypropylenepolyoxyethylene glycol having an average molecular weight of 3,500.

4. A process as described in claim 1, wherein after conclusion of the reaction, unreacted substance contained in the reaction mixture is removed by means of anion exchanger chromatography, followed by recovery of the resulting modified superoxide dismutanse with a high degree of purity.

5. A process as described in claim 1, wherein the water soluble polymer is a monomethoxypolyoxyethylene glycol having an average molecular weight of 3,500.

6. A process as described in claim 1, wherein the water soluble polymer is a monomethoxypolyoxyethylene.polyoxypropylene glycol.polyoxyethylene glycol having an average molecular weight of 3,500.

7. A process as described in claim 1 wherein the concentration of the buffer is 0.2 to 0.4M.

8. A process as described in claim 1 wherein the concentration of the water-soluble polyalkylene polymer is 0.25 to 0.3M.

9. A process as described in claim 1 wherein the concentration ratio of the water-soluble polyalkylene polymer to the carbonyldiimidazole is 1:1.5 to 1:2.5.

* * * * *